(12) United States Patent
Wright (10) Patent No.: US 8,197,447 B2
(45) Date of Patent: Jun. 12, 2012

(54) FLEXIBLE IV SITE PROTECTOR

(75) Inventor: Clifford A. Wright, San Diego, CA (US)

(73) Assignee: Venetec International, Inc., Covington, GA (US)

( * ) Notice: Subject to any disclaimer, the term of this patent is extended or adjusted under 35 U.S.C. 154(b) by 973 days.

(21) Appl. No.: 11/110,986

(22) Filed: Apr. 19, 2005

(65) Prior Publication Data

US 2006/0247577 A1 Nov. 2, 2006

(51) Int. Cl.
*A61M 5/32* (2006.01)
(52) U.S. Cl. ........ 604/174; 604/179; 604/192; 604/263; 128/846; 128/888
(58) Field of Classification Search .......... 128/846, 128/888, DIG. 6, DIG. 26; 604/174, 179, 604/192, 263
See application file for complete search history.

(56) References Cited

U.S. PATENT DOCUMENTS

| | | | |
|---|---|---|---|
| 695,270 A * | 3/1902 | Beringer | 128/888 |
| 1,706,634 A | 3/1928 | Seils | |
| 2,008,340 A * | 7/1935 | Salvati et al. | 604/174 |
| 2,367,690 A | 7/1943 | Purdy | |
| 2,402,306 A * | 6/1946 | Turkel | 604/174 |
| 3,046,984 A | 7/1962 | Eby | |
| 3,194,235 A | 7/1965 | Cooke | |
| 3,461,869 A * | 8/1969 | Hargest | 604/175 |
| 3,537,452 A * | 11/1970 | Wilks | 604/162 |
| 3,568,679 A | 3/1971 | Reif | |
| 3,630,195 A | 12/1971 | Santomieri | |
| 3,640,275 A * | 2/1972 | Burke et al. | 604/177 |
| 3,782,383 A * | 1/1974 | Thompson et al. | 604/177 |
| 3,826,254 A | 7/1974 | Mellor | |
| 3,900,026 A | 8/1975 | Wagner | |
| 3,901,226 A | 8/1975 | Scardenzan | |
| 3,910,538 A | 10/1975 | Baitella | |
| 4,059,105 A | 11/1977 | Cutruzzula et al. | |
| 4,082,094 A | 4/1978 | Dailey | |
| 4,129,128 A | 12/1978 | McFarlane | |
| D252,822 S | 9/1979 | McFarlane | |
| 4,193,174 A | 3/1980 | Stephens | |
| 4,224,937 A | 9/1980 | Gordon | |
| 4,250,880 A | 2/1981 | Gordon | |
| 4,277,102 A | 7/1981 | Aras | |
| 4,316,461 A | 2/1982 | Marais et al. | |

(Continued)

FOREIGN PATENT DOCUMENTS

CA 1 311 977 12/1992

(Continued)

OTHER PUBLICATIONS

U.S. Appl. No. 09/136,271, applicant Steven F. Bierman, filed Aug. 18, 1998.

(Continued)

*Primary Examiner* — Jackie Ho
*Assistant Examiner* — Scott Medway
(74) *Attorney, Agent, or Firm* — Knobbe Martens Olson & Bear LLP (57) ABSTRACT

A venipuncture site protector that includes a securement and a cover mounted to said securement. The cover includes a proximal end having a front wall with a tube receiving slot. The cover also includes a distal end having an arch that forms an opening that lies on a vertical plane that is substantially perpendicular to the securement.

19 Claims, 11 Drawing Sheets

U.S. PATENT DOCUMENTS

| | | | |
|---|---|---|---|
| 4,333,468 A | 6/1982 | Geist | |
| 4,470,410 A | 9/1984 | Elliott | |
| 4,484,913 A | 11/1984 | Swauger | |
| 4,516,968 A | 5/1985 | Marshall et al. | |
| 4,517,971 A | 5/1985 | Sorbonne | |
| 4,563,177 A | 1/1986 | Kamen | |
| 4,585,443 A * | 4/1986 | Kaufman | 604/174 |
| 4,627,842 A * | 12/1986 | Katz | 604/177 |
| 4,632,670 A | 12/1986 | Muller | |
| 4,633,863 A | 1/1987 | Filips et al. | |
| 4,645,492 A | 2/1987 | Weeks | |
| 4,666,434 A * | 5/1987 | Kaufman | 604/179 |
| 4,667,666 A | 5/1987 | Fryslie | |
| 4,669,458 A | 6/1987 | Abraham | |
| 4,679,553 A | 7/1987 | Proulx | |
| 4,711,636 A | 12/1987 | Bierman | |
| 4,737,143 A | 4/1988 | Russell | |
| 4,781,695 A | 11/1988 | Dalton | |
| 4,846,807 A | 7/1989 | Safadago | |
| 4,852,844 A | 8/1989 | Villaveces | |
| 4,863,432 A | 9/1989 | Kvalo | |
| 4,870,976 A | 10/1989 | Denny | |
| 4,878,897 A * | 11/1989 | Katzin | 604/86 |
| 4,898,587 A | 2/1990 | Mera | |
| 4,913,393 A | 4/1990 | Wood | |
| 4,976,698 A | 12/1990 | Stokley | |
| 4,997,421 A | 3/1991 | Palsrok et al. | |
| 5,029,941 A | 7/1991 | Twisselmann | |
| 5,037,397 A | 8/1991 | Kalt et al. | |
| 5,074,847 A | 12/1991 | Greenwell et al. | |
| 5,084,026 A | 1/1992 | Shapiro | |
| 5,112,313 A | 5/1992 | Sallee | |
| 5,116,324 A | 5/1992 | Brierley et al. | |
| 5,137,519 A | 8/1992 | Littrell et al. | |
| 5,167,240 A | 12/1992 | Rozier et al. | |
| 5,192,273 A | 3/1993 | Bierman | |
| 5,192,274 A | 3/1993 | Bierman | |
| 5,215,532 A | 6/1993 | Atkinson | |
| 5,230,350 A | 7/1993 | Fentress | |
| 5,238,010 A | 8/1993 | Grabenkort | |
| 5,281,001 A | 1/1994 | Bergsten et al. | |
| 5,290,248 A | 3/1994 | Bierman et al. | |
| D347,060 S | 5/1994 | Bierman | |
| 5,314,411 A | 5/1994 | Bierman et al. | |
| 5,328,487 A | 7/1994 | Starchevich | |
| 5,339,834 A | 8/1994 | Marcelli | |
| 5,354,282 A | 10/1994 | Bierman | |
| 5,356,391 A | 10/1994 | Stewart | |
| 5,370,627 A | 12/1994 | Conway | |
| 5,395,344 A | 3/1995 | Beisang et al. | |
| 5,407,249 A | 4/1995 | Bonutti | |
| 5,413,120 A | 5/1995 | Grant | |
| 5,413,562 A | 5/1995 | Swauger | |
| D359,120 S | 6/1995 | Sallee et al. | |
| 5,449,349 A | 9/1995 | Sallee et al. | |
| D363,543 S * | 10/1995 | Van Funderburk et al. | D24/130 |
| 5,456,671 A | 10/1995 | Bierman | |
| 5,462,247 A | 10/1995 | Aldrich | |
| D364,922 S | 12/1995 | Bierman | |
| 5,480,719 A | 1/1996 | Tollini | |
| D375,355 S | 11/1996 | Bierman | |
| D375,356 S | 11/1996 | Bierman | |
| 5,577,516 A | 11/1996 | Schaeffer | |
| 5,578,013 A | 11/1996 | Bierman | |
| D377,125 S | 1/1997 | Adamsson | |
| D377,831 S | 2/1997 | Bierman | |
| 5,605,546 A | 2/1997 | Wolzinger et al. | |
| 5,664,581 A | 9/1997 | Ashley | |
| 5,681,290 A | 10/1997 | Alexander | |
| 5,685,859 A | 11/1997 | Kornerup | |
| 5,686,096 A | 11/1997 | Khan et al. | |
| 5,690,616 A | 11/1997 | Mogg | |
| 5,693,032 A | 12/1997 | Bierman | |
| 5,702,371 A | 12/1997 | Bierman | |
| 5,713,591 A | 2/1998 | Zarkhin et al. | |
| 5,722,959 A | 3/1998 | Bierman | |
| 5,728,053 A | 3/1998 | Calvert | |
| 5,733,571 A | 3/1998 | Sackler | |
| 5,776,106 A | 7/1998 | Matyas | |
| 5,800,402 A | 9/1998 | Bierman | |
| 5,800,410 A | 9/1998 | Gawreluk | |
| 5,810,781 A | 9/1998 | Bierman | |
| D399,954 S | 10/1998 | Bierman | |
| 5,827,230 A | 10/1998 | Bierman | |
| 5,827,239 A | 10/1998 | Dillon et al. | |
| D401,330 S * | 11/1998 | Wright-Owens | D24/128 |
| 5,833,666 A | 11/1998 | Davis et al. | |
| 5,833,667 A | 11/1998 | Bierman | |
| 5,855,591 A | 1/1999 | Bierman | |
| 5,885,254 A | 3/1999 | Matyas | |
| 5,897,519 A | 4/1999 | Shesol et al. | |
| 6,050,934 A | 4/2000 | Mikhail et al. | |
| D425,619 S | 5/2000 | Bierman | |
| 6,096,943 A | 8/2000 | Maiwald | |
| 6,099,509 A | 8/2000 | Brown et al. | |
| 6,113,577 A | 9/2000 | Hakky et al. | |
| 6,123,690 A * | 9/2000 | Mejslov | 604/533 |
| 6,132,398 A | 10/2000 | Bierman | |
| 6,132,399 A | 10/2000 | Shultz | |
| 6,213,979 B1 | 4/2001 | Bierman | |
| 6,224,571 B1 | 5/2001 | Bierman | |
| 6,231,547 B1 | 5/2001 | O'Hara | |
| 6,231,548 B1 | 5/2001 | Bassett | |
| 6,241,697 B1 | 6/2001 | Augustine | |
| 6,255,552 B1 | 7/2001 | Cummings et al. | |
| 6,258,066 B1 | 7/2001 | Urich | |
| 6,264,977 B1 | 7/2001 | Hoffmann | |
| 6,283,945 B1 | 9/2001 | Bierman | |
| 6,290,676 B1 | 9/2001 | Bierman | |
| 6,322,539 B1 | 11/2001 | Cook | |
| 6,332,874 B1 * | 12/2001 | Eliasen et al. | 604/174 |
| 6,361,523 B1 | 3/2002 | Bierman | |
| 6,375,639 B1 | 4/2002 | Duplessie | |
| 6,413,240 B1 | 7/2002 | Bierman | |
| 6,428,515 B1 | 8/2002 | Bierman | |
| 6,428,516 B1 | 8/2002 | Bierman | |
| 6,436,073 B1 | 8/2002 | Teichert | |
| 6,447,485 B2 | 9/2002 | Bierman | |
| 6,447,486 B1 | 9/2002 | Tollini | |
| 6,458,104 B2 * | 10/2002 | Gautsche | 604/179 |
| 6,471,676 B1 | 10/2002 | DeLegge et al. | |
| 6,482,183 B1 | 11/2002 | Pausch | |
| 6,491,664 B2 | 12/2002 | Bierman | |
| 6,500,154 B1 | 12/2002 | Hakky et al. | |
| D469,530 S | 1/2003 | Gomez | |
| D470,936 S | 2/2003 | Bierman | |
| 6,517,522 B1 | 2/2003 | Bell et al. | |
| 6,526,981 B1 * | 3/2003 | Rozier et al. | 128/846 |
| 6,551,285 B1 | 4/2003 | Bierman | |
| 6,572,588 B1 | 6/2003 | Bierman et al. | |
| 6,582,403 B1 | 6/2003 | Bierman et al. | |
| 6,616,635 B1 | 9/2003 | Bell et al. | |
| 6,619,598 B2 | 9/2003 | De Miranda | |
| 6,619,747 B2 | 9/2003 | Ko et al. | |
| 6,626,890 B2 | 9/2003 | Nguyen et al. | |
| 6,652,487 B1 | 11/2003 | Cook | |
| 6,663,600 B2 | 12/2003 | Bierman et al. | |
| 6,689,104 B2 | 2/2004 | Bierman | |
| D492,411 S | 6/2004 | Bierman | |
| 6,770,055 B2 | 8/2004 | Bierman et al. | |
| 6,786,892 B2 | 9/2004 | Bierman | |
| 6,809,230 B2 | 10/2004 | Hancock et al. | |
| 6,827,705 B2 | 12/2004 | Bierman | |
| 6,827,706 B2 | 12/2004 | Tollini | |
| 6,827,707 B2 | 12/2004 | Wright et al. | |
| 6,834,652 B2 | 12/2004 | Altman | |
| 6,837,875 B1 | 1/2005 | Bierman | |
| 6,855,135 B2 | 2/2005 | Lockwood et al. | |
| 6,866,652 B2 | 3/2005 | Bierman | |
| D503,977 S | 4/2005 | Bierman | |
| 6,951,550 B2 | 10/2005 | Bierman | |
| 6,972,003 B2 | 12/2005 | Bierman | |
| 6,979,320 B2 | 12/2005 | Bierman | |
| 6,981,969 B2 | 1/2006 | Chavez et al. | |
| 7,014,627 B2 | 3/2006 | Bierman | |
| 7,018,362 B2 | 3/2006 | Bierman | |
| 7,070,580 B2 | 7/2006 | Nielsen | |

| | | |
|---|---|---|
| 7,090,660 B2 | 8/2006 | Roberts et al. |
| D528,206 S | 9/2006 | Bierman |
| 7,153,291 B2 | 12/2006 | Bierman |
| 7,155,287 B2 * | 12/2006 | Gavronsky ............ 607/46 |
| 7,354,421 B2 | 4/2008 | Bierman |
| 2001/0011164 A1 | 8/2001 | Bierman |
| 2002/0068904 A1 | 6/2002 | Bierman et al. |
| 2002/0099360 A1 | 7/2002 | Bierman |
| 2003/0055382 A1 | 3/2003 | Schaeffer |
| 2003/0069529 A1 | 4/2003 | Augustine et al. |
| 2003/0229313 A1 | 12/2003 | Bierman |
| 2004/0102736 A1 | 5/2004 | Bierman |
| 2004/0111067 A1 | 6/2004 | Kirchhofer |
| 2004/0138624 A1 | 7/2004 | Bierman |
| 2004/0143220 A1 | 7/2004 | Worthley |
| 2004/0158209 A1 | 8/2004 | Wright |
| 2004/0204685 A1 | 10/2004 | Wright et al. |
| 2005/0182367 A1 | 8/2005 | Walborn |
| 2005/0215953 A1 | 9/2005 | Rossen |
| 2005/0288635 A1 | 12/2005 | Davis et al. |
| 2006/0015076 A1 | 1/2006 | Heinzerling et al. |
| 2006/0064063 A1 | 3/2006 | Bierman |
| 2006/0135944 A1 | 6/2006 | Bierman |
| 2006/0184127 A1 | 8/2006 | Bierman |
| 2006/0184129 A1 | 8/2006 | Bierman |
| 2006/0217669 A1 | 9/2006 | Botha |
| 2006/0247577 A1 | 11/2006 | Wright |
| 2006/0264836 A1 | 11/2006 | Bierman |
| 2006/0270995 A1 | 11/2006 | Bierman |
| 2009/0048563 A1 | 2/2009 | Ethelfeld et al. |

FOREIGN PATENT DOCUMENTS

| | | |
|---|---|---|
| CA | 1 318 824 | 6/1993 |
| EP | 0356683 | 3/1990 |
| EP | 0356683 | 3/2000 |
| WO | WO 94/21319 | 9/1994 |
| WO | WO 97/15337 | 5/1997 |
| WO | WO 99/55409 | 11/1999 |

OTHER PUBLICATIONS

International Search Report for App. No. PCT/US03/25622, mailed Mar. 10, 2004.

Venetec Statlock Instructional Sheets; statlock.com/products.html; "IV Select; IV Ultra; IV Plus; IV; Intima; IV-K; Arterial Plus; CV Plus; CV Ultra; The Advantages of Statlock for Extended-Dwell Catheters; PICC Plus Patient User Guide;".

* cited by examiner

FLEXIBLE IV SITE PROTECTOR

FIELD OF THE INVENTION

The present invention relates to a device for protecting an intravenous site of a patient from water and other contaminants during intravenous infusion and more particularly to a device for securing and protecting an intravenous catheter from unwanted and undesired movement thereby significantly decreasing complications and reducing unscheduled catheter restarts.

BACKGROUND

IV's have become a widely used and standard technique to introduce a substance into a vein of an individual. The substance can be introduced rapidly by an intravenous injection, or slowly by an intravenous infusion. IV's are typically used to introduce or administer blood or plasma during a blood transfusion; a mixture of glucose (sugar) and saline (salt) or other varied or concentrated nutrients for artificial feeding or hydration; and various drugs or medicines to treat pain, illness or disease.

IV's are typically comprised of a bag or bottle, a tube and a cannula. The bag or bottle store and contain the substance that is to be administered to the individual and is suspended from a holder above the insertion point of the IV. The tube is generally made of clear plastic for easy examination. The tube is connected at one end to the bag or bottle suspended from the holder. The opposite end of the tube is connected to the cannula. The cannula is inserted into the vein of the individual through the skin at the insertion point. After the cannula is inserted into the vein and connected to the tube, it is generally secured in place by surgical tape to the skin surrounding the insertion point. The cannula is secured in place to prevent damage which could otherwise result from its movement relative to the vein or insertion point through the skin.

An intravenous catheter can be dangerous if not properly secured—dangerous to both the patient and the healthcare worker. Taping the intravenous catheter to the skin of the patient is not an acceptable solution, as tape is not designed to secure a catheter. Moreover, tape allows micro-movement of a catheter which in turn can result in complications, including phlebitis, infiltration, extravasations, dislodgement, disconnection, and even infection. Such complications necessitate unscheduled catheter restarts—which expose healthcare workers to dangerous blood-filled stylets and needles.

An improper angle of insertion can also be dangerous to the patient and can lead to complications such as those described above, particularly phlebitis. Not all insertion sites have the same amount of tissue or flesh surrounding a vein. Therefore, applicant has discovered that a uniform angle of insertion for all sites is not an optimal solution. Moreover, improper insertion angle is difficult to remedy with current application methods.

Therefore it would be highly desirable to have a new and improved device and method for securing an intravenous catheter from unwanted and undesired movement thereby significantly decreasing complications and reducing unscheduled catheter restarts.

SUMMARY OF THE INVENTION

In accordance with one embodiment, there is provided a venipuncture site protector that includes a securement, a cover mounted on the securement, and an internal wall that divides the cover into a catheter receiving portion and a tube receiving portion. The internal wall includes a tube access channel. The cover includes a proximal end having a front wall with a tube receiving slot. The cover also includes a distal end that forms an arch. The tube receiving slot and tube access channel are in substantial alignment with one another.

In accordance with another embodiment, there is provided a venipuncture site protector that includes a securement and a cover mounted to said securement. The cover includes a proximal end having a front wall with a tube receiving slot. The cover also includes a distal end having an arch that forms an opening that lies on a vertical plane that is substantially perpendicular to the securement.

BRIEF DESCRIPTION OF THE DRAWINGS

The above mentioned features and steps of the invention and the manner of attaining them will become apparent, and the invention itself will be best understood by reference to the following description of the embodiments of the invention in conjunction with the accompanying drawings wherein.

DETAILED DESCRIPTION OF THE PREFERRED EMBODIMENTS

Before discussing the preferred embodiment of the present invention, it may be helpful to first briefly review the basic devices and concepts used in the administration of fluids and or medications directly into a venous system of a patient, which is otherwise called, intravenous therapy, or simply I.V. therapy.

The most common method of administering I.V. fluids is with an I.V. catheter 8, which generally comprises a catheter C, a needle (not shown), and a catheter head or flashback chamber H which is adapted to be connected to an I.V. set and its associated I.V. tubing T by a luer nut arrangement L. The flowing of blood into the flashback chamber H provides an I.V. technician with a visual indication of a successful venous entry.

Figure 1:
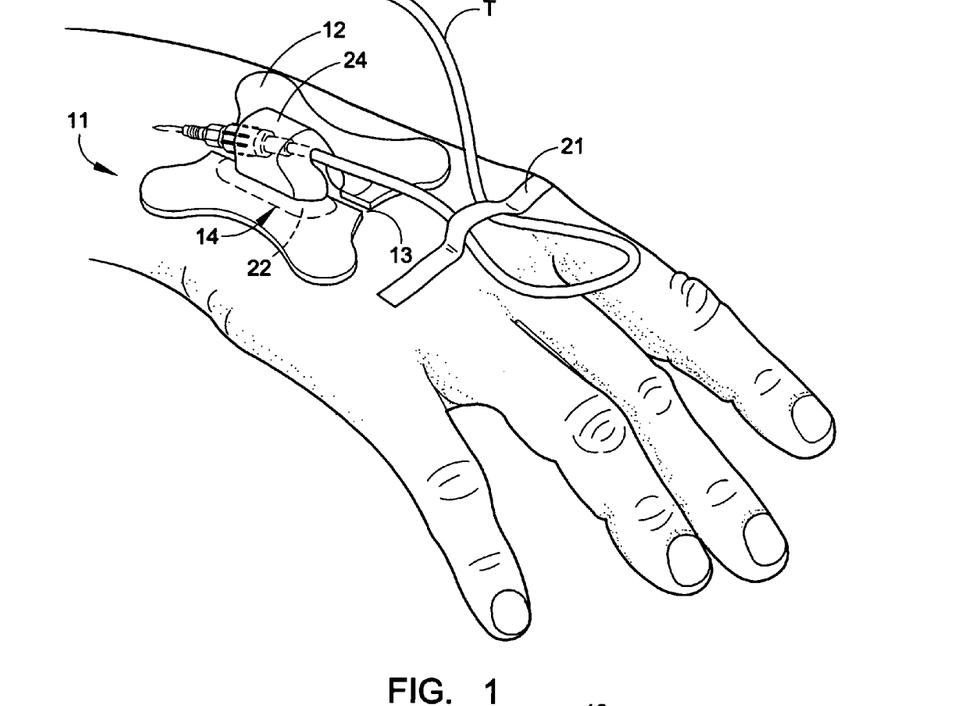
FIG. 1 is a perspective view of a venipuncture site protector, which is constructed in accordance with the present invention.

In use the I.V. technician selects a venous access site, which typically will be the top surface area of a patient's hand as best seen in FIG. 1. Once the I.V. technician has selected and disinfected the venous access site area, the catheter C is then inserted into a located vein within the site area using the needle. The needle is then withdrawn leaving only the semi-flexible catheter C in the vein of the patient. Blood flow into the flashback chamber H provides the I.V. technician with a visual indication that the catheter C has been properly positioned within the vein of the patient.

The I.V. technician then attaches an I.V. fluid set (not shown) and more particularly, the I.V. tubing T to the catheter head H using the luer lock nut arrangement L disposed at the distal end of the I.V. tubing T. The luer lock nut arrangement L includes a catheter connector 9 that is secured to the distal end of the tubing T and which is adapted to be inserted into the flashback chamber H and then locked into a fluid tight seal with a rotatable nut N that slide along the outer surface of the catheter connector 9. In this regard, the connector 9 is inserted into the flashback chamber H and the nut N is pushed along the connector 9 and onto the proximal end of the head H. With the nut N so positioned against the head H, the nut N is rotated into locking engagement. In this process, the I.V. tubing T is connected in a fluid tight seal with the catheter C to facilitate the administration of fluid therapy.

It should be understood by those skilled in the art that the I.V. connector 9 and I.V. catheter 8 are standardized relative to relative to size and overall length. This standardization of size and length is important relative to the preferred embodiment of the present invention as will be explained hereinafter in greater detail.

Figure 2:
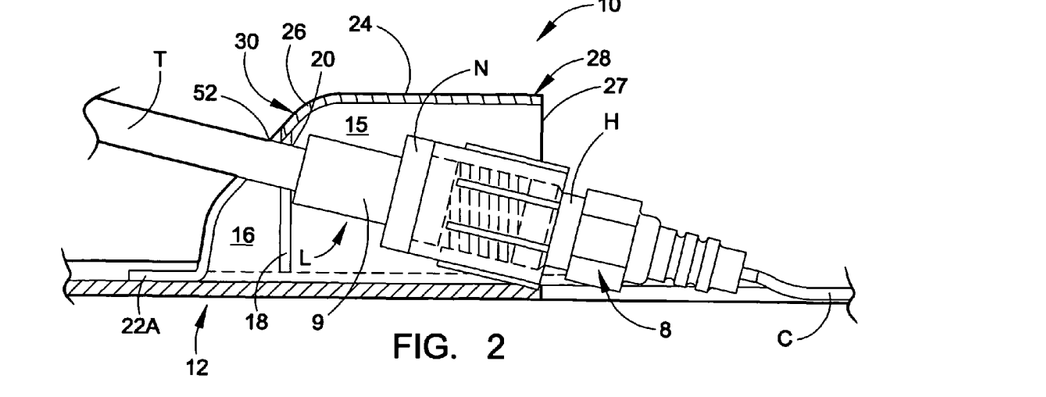
FIG. 2 is side elevational view of the venipuncture site protector of FIG. 1.

Referring now to the drawings and more particularly to FIGS. 1 and 2 thereof there is shown a venipuncture site protector or shielding device 10, which is constructed in accordance with one preferred embodiment of the present invention. The venipuncture site protector 10 is adapted to protect a venipuncture site, and more particularly an I.V. connected catheter 8 from unwanted and undesired movement thereby significantly decreasing complications and reducing unscheduled catheter restarts. The term "I.V. connected catheter" as used herein means the catheter connector 9, the luer lock nut N, the catheter head H, and the exposed proximal end of the catheter C connected at the distal end of the catheter head H, which catheter C was previously inserted into the vein of a patient.

Considering now the venipuncture site protector 10 in greater detail with reference to FIGS. 1-5, the venipuncture site protector 10 generally includes a slotted securement 12 having a slotted partitioned transparent shield, cover or body member 14 and a removable protective backing or cover 17 secured thereto. The cover 14 has an overall length 1, height h, and width dimension w, which dimensions are selected to assure that: 1) a conventional intravenous catheter head H and its associated catheter C (that has been previously disposed into a vein of a patient) and 2) the luer lock arrangement L of an I.V. set (previously connected to the catheter head H) are generally underneath the cover 14 and thereby, are protected from accidental contact with an object. As will be explained hereinafter in greater detail, the slotted securement 12 and the slotted partitioned cover 14 cooperate to permit the I.V. connected catheter 8 to be wedged in a friction tight manner against a slotted internal wall 18 disposed within the cover 14 and to releasably capture the I.V. tubing T so that it becomes extremely difficult, if not impossible, to move the I.V. connected catheter without first removing the securement 12 from the skin of the patient.

Figures 3, 4:
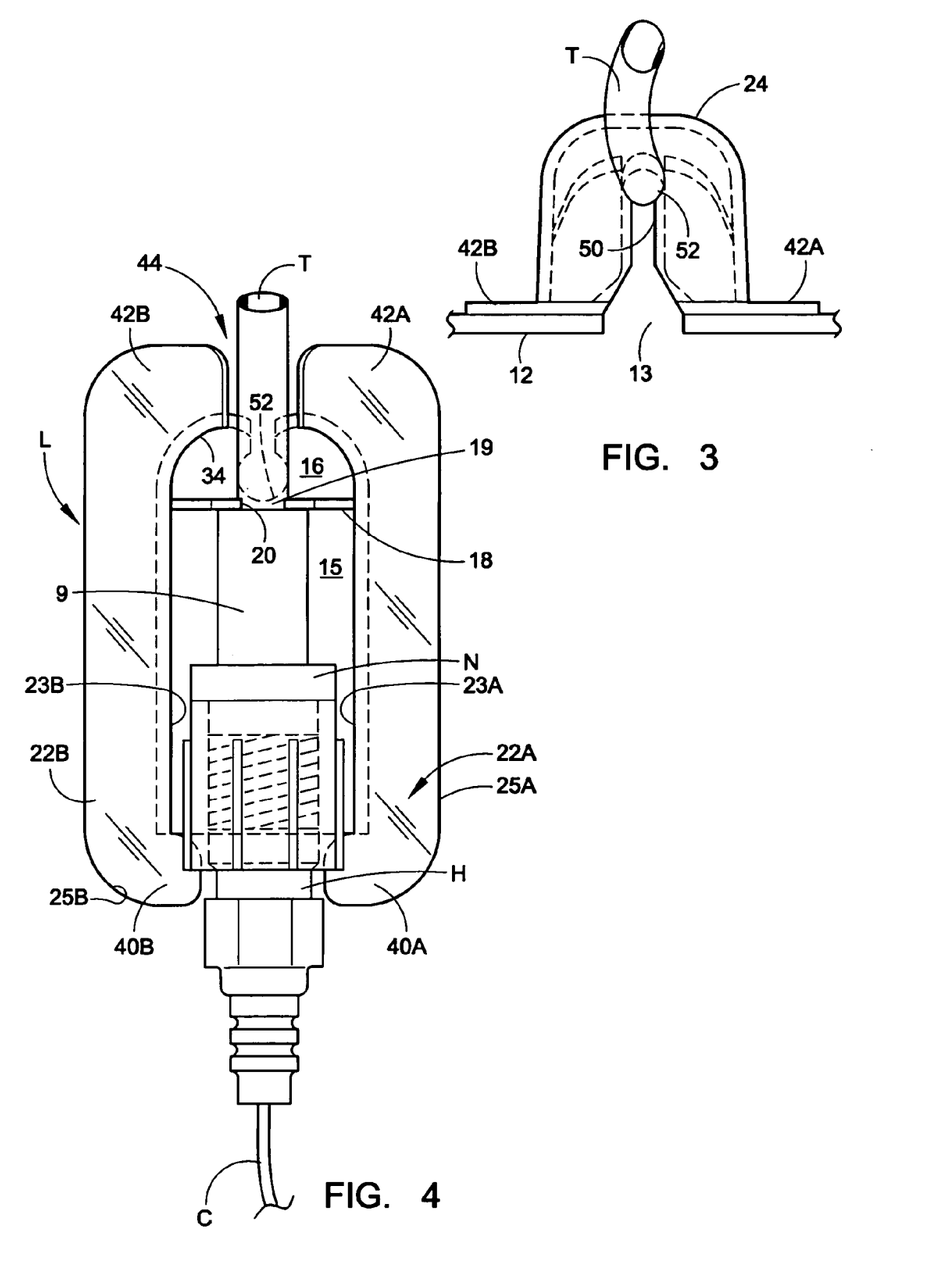
FIG. 3 is front elevational view of the venipuncture site protector of FIG. 1.
FIG. 4 is a bottom plane view of a protective cover illustrated in FIG. 2.
Figure 27:
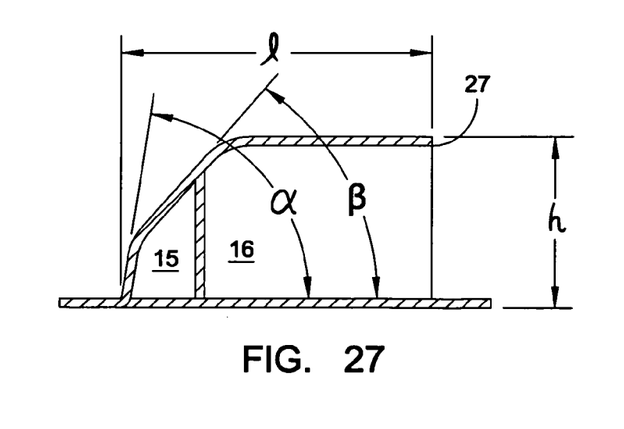
FIG. 27 is a diagrammatic side elevational sectional view of the venipuncture site protector of FIG. 1.

The body member 14 as best seen in FIGS. 2, 4 and 27 has a unitary construction which is defined by a pair of parallel flanges 22A and 22B each having inner edges 23A and 23B and outer edges 25A and 25B respectively, and a vault 24 which is integrally connected to the flanges 22A and 22B rising upwardly from the inner edges 23A and 23B of the flanges to an apex or roof 26 of the vault 24 (FIG. 2).

The flanges 22A and 22B each has a distal portion 40A and 40B and a proximal portion 42A and 42B respectively, which proximal portions 42A and 42B converge to form a tube access slot 44 that is in alignment with another tube access slot 13 that is disposed in a proximal portion of the securement 12.

The vault 24 is generally trapezoidal or pentagonal in a side elevational view (FIG. 2) defined by a distal end having an arch 27 forming an opening 28 and a proximal end forming a sloped wall 30. The sloped wall 30 and the arch 27 extend upwardly from the flanges 22A and 22B meeting at the apex 26. As best seen in FIGS. 3-4, the sloped proximal wall 30 includes a tube access slot 50 that extends partially up the wall 30 terminating in a tube stop 52. As best seen in the top plane view of FIG. 4, the tube access slot 50 is in alignment with the tube access slot 44 (formed by the convergence of the proximal portions 42A and 42B of the flanges 22A and 22B) and the tube access slot 13 of the securement 12.

Depending perpendicularly downwardly from the ceiling of the sloped proximal wall 30 is an internal wall 18 whose side peripheral edges are integrally connected to an interior surface portion of the sloped proximal wall 30. The internal wall 18 divides or partitions the interior space of the body member 14 into a distal portion or I.V. connected catheter receiving compartment or portion 15 and a proximal space or I.V. tube receiving portion or compartment 16. The internal wall 18 includes a centrally disposed tube receiving slot 19 that terminates at its upper end in a tube receiving stop 20, which is generally circular, and dimensioned for receiving therein the tubing T of the I.V. set. As best seen in FIGS. 2 and 4, the tube receiving stop 20 is also in general parallel alignment with the tube receiving stop 52 disposed in the front wall 30. In this regard, the two stops 20 and 52 are slightly spaced apart from one another with the stop 20 being vertically lower than the stop 52. The spacing helps to secure the tubing T of the I.V. set at two different points, one point at the internal wall 18 completely enclosed within the vault 24 and another point at the front wall 30 of the vault 24 so the tubing T cannot be easily dislodged once it is captured in the stops 20 and 52 as will be explained hereinafter in greater detail.

Considering now the securement 12 in greater detail with reference to FIGS. 5A, 5B, 19, 20 and 21, the securement 12 generally includes a base securement 120 with a centrally disposed plug 160, which is adhesively secured to the base securement 120. The plug 160 as will be explained hereinafter in greater detail is utilized to help secure the dome 24 to the base securement 120.

Figure 5A:
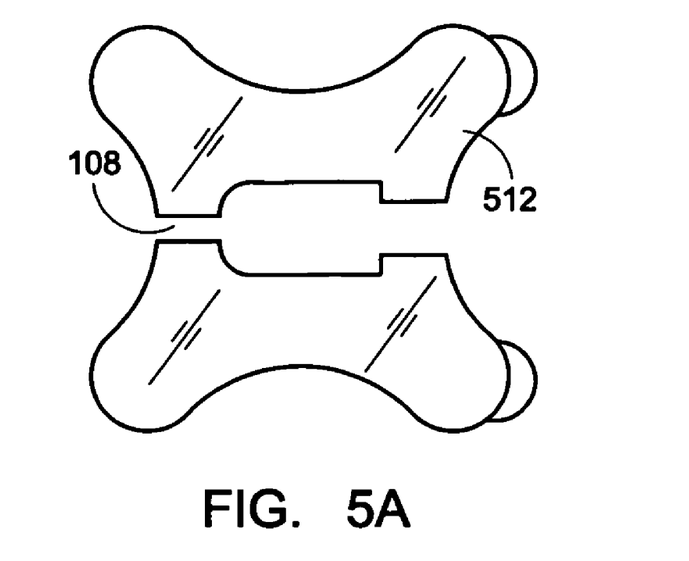
FIG. 5A is a top plane view of a securement forming part of the venipuncture site protector of FIG. 1.
Figure 17:
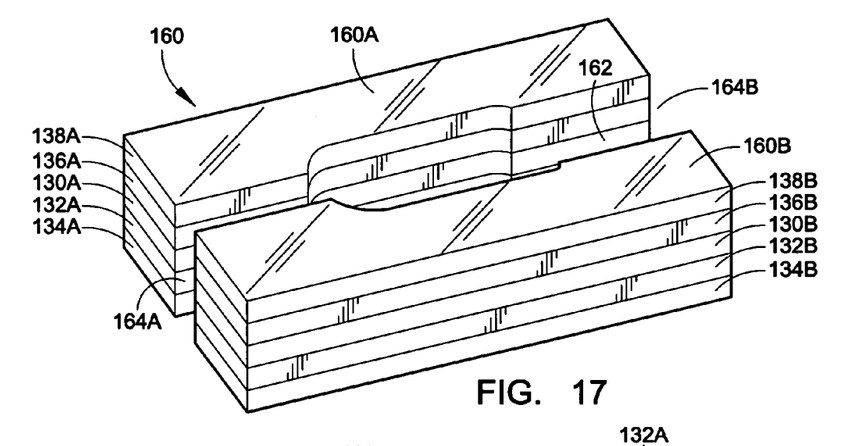

In one embodiment, as shown in FIG. 5A, the securement is a unibody structure in which the wings are connected at one end. The base securement 120 includes an access channel 108. The access channel is aligned with a similar access channel that is disposed at one end of a plug, such as the plug shown in FIG. 17 or a similar plug with a unibody design rather than a two piece design as shown in FIG. 17. The access channel 108 and the access channel of the plug cooperate to define the tube access channel or slot 13.

Figure 5B:
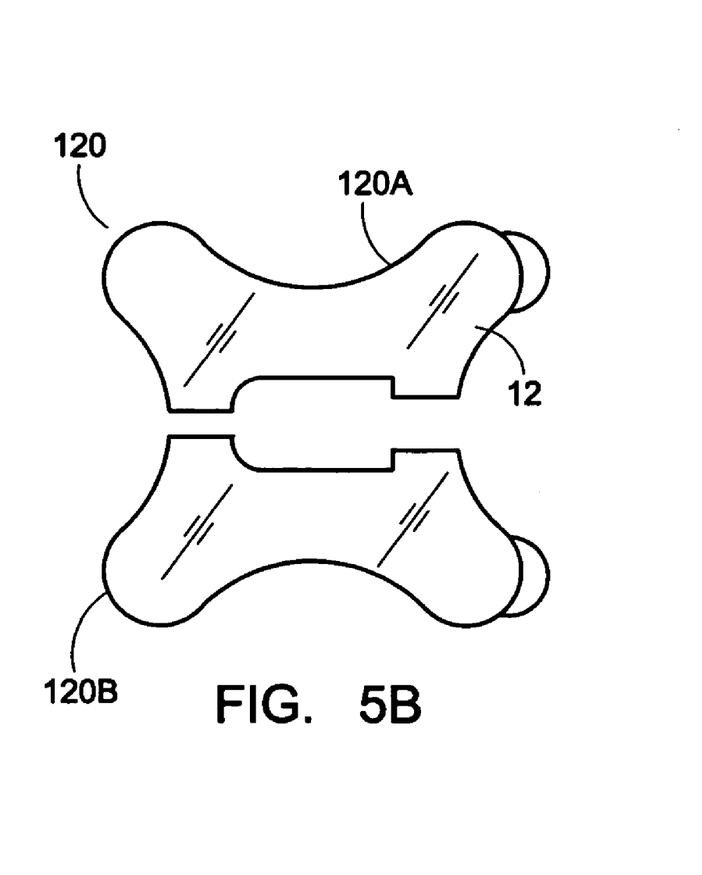
FIG. 5B is a top plane view of another type of securement configuration for use with the protective cover of FIG. 4.
Figures 10, 11:
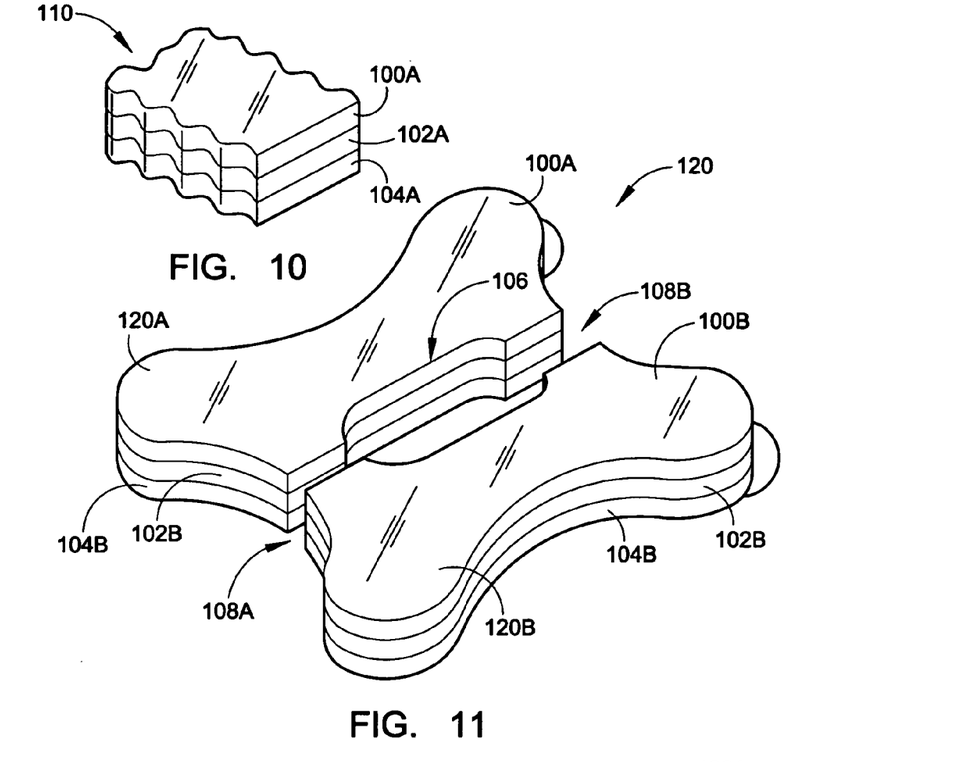
FIGS. 10-22 illustrate the steps of making the venipuncture site protector of FIG. 1.
Figure 12:
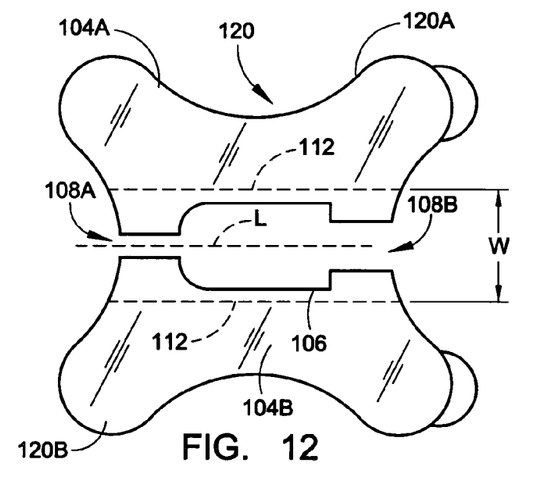
Figure 13:
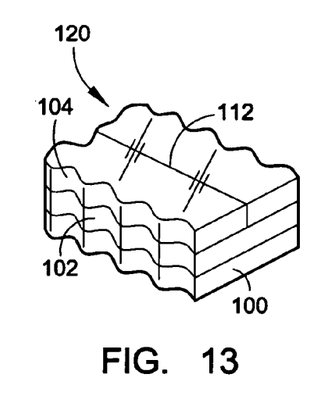

In another embodiment, as shown in FIGS. 5B and 11, the base securement 120 has a two piece configuration forming two opposing wings 120A and 120B. In the configuration shown in FIG. 11, each wing has a smooth plastic layer 100A and 100B, and each of the smooth plastic layers 100A and 100B is coated on its underside with a layer of non-skin irritating adhesive 102A and 102B respectively. As shown in FIG. 17, the plug 160 can also include a two piece configuration forming two opposing plugs 160A and 160B, each of which has an underside coated with a layer of non-skin irritating adhesive 136A and 136B respectively. The adhesive layer 102A and 102B disposed on the wings 120A and 120B of the base securement 120 is covered by a pair of spaced apart wax paper covers 104A and 104B, while the adhesive layer 136A and 136B disposed on the plugs 160A and 160B, is covered by another sheet of wax paper 17. In one embodiment, as shown in FIG. 11, the base securement 120 includes an access channel 108A, which is aligned with a similar access channel 164A that is disposed at one end of the plug 160, and a second access channel 108B at the other end of the securement 120, which is aligned with a similar access channel 164B that is disposed at the other end of the plug 160. The access channels 108A and 164A cooperate to define the tube access channel or slot 13. The access channels 108B and 164B cooperate to form a distal access channel for a catheter, which is larger than the channel formed by access channels 108A and 164A.

The protective covers 17 and 104A and 104B are removable and are provided to protect the adhesive surfaces 136A and 136B and 102A and 102B respectively until such time as the securement 120 is ready to be utilized with a patient. It will suffice for the moment to mention that the securement 12 is initially or partially secured to the venipuncture site 11 by removing the cover 17 and pressing the adhesive layers 136A and 136B against the skin of the patient and then after the I.V. connected catheter has been secured within the vault 24, the securement 12 is fixed in placed by removing the covers 104A and 104B to press the uncovered adhesive surfaces 102A and 102B against the skin of the patient. This is an important feature of this embodiment of the present invention, as this allows the site protector 10 to remain in place for extended periods of time thereby greatly reducing the risk of exposing healthcare workers to dangerous blood-filled stylets and needles.

Figure 21:
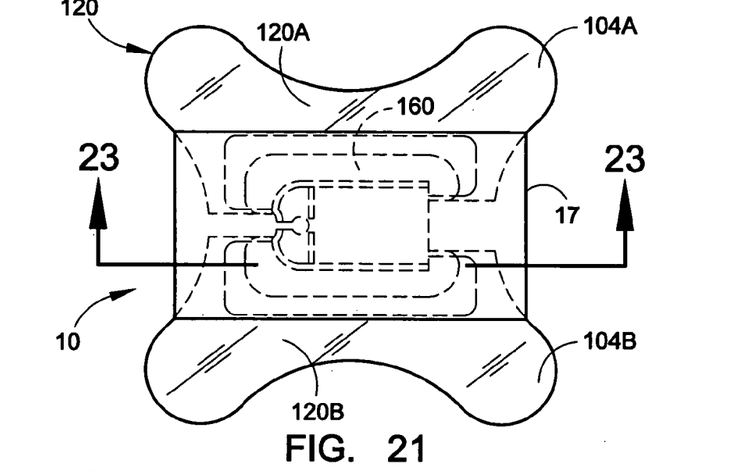
Figures 24, 25:
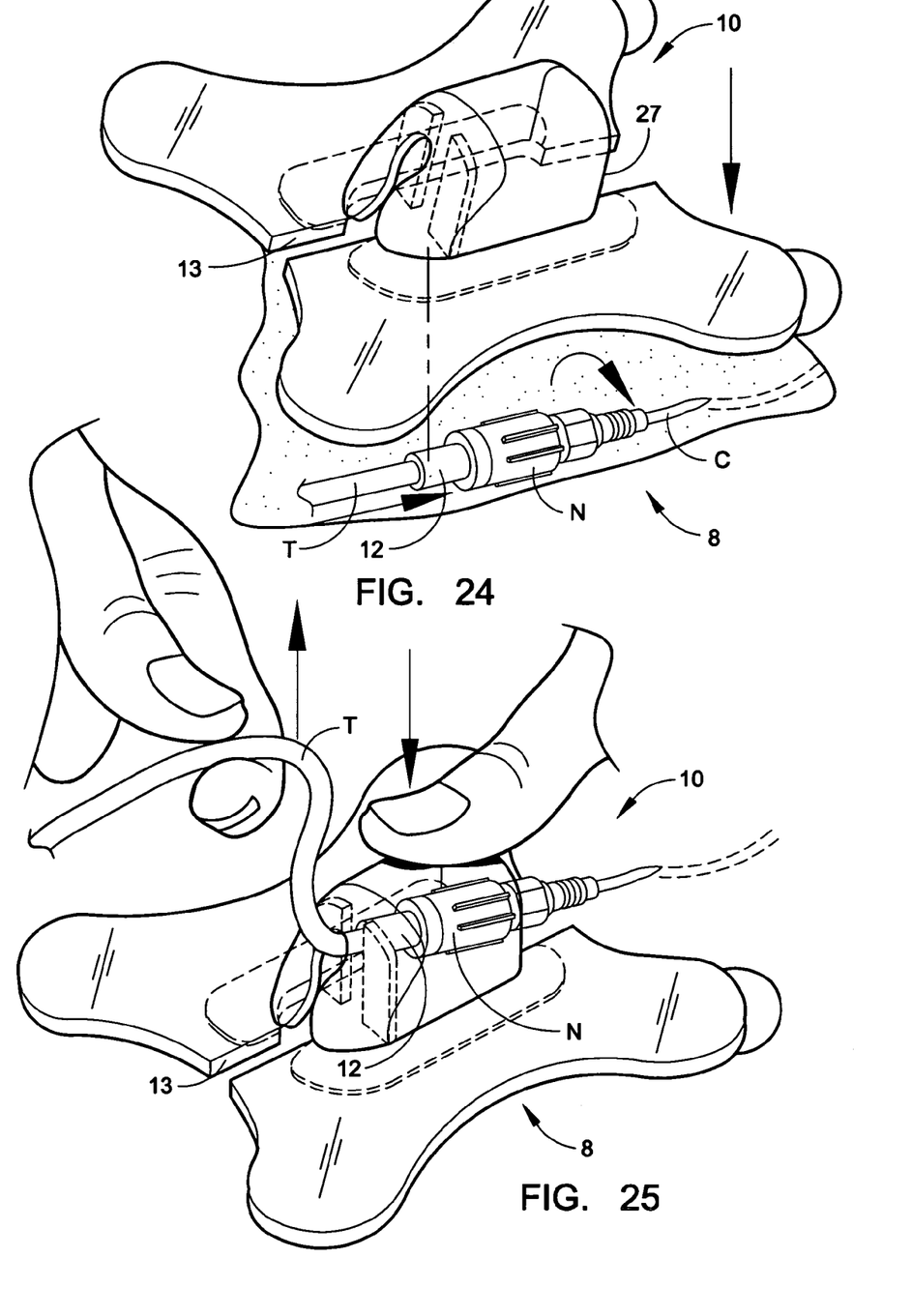
FIGS. 24-26 illustrate the steps of using the venipuncture site protector of FIG. 1.

Considering now the novel method of using the site protector 10, as best seen in FIGS. 21 and 24-25, a healthcare provider such as a doctor or a nurse creates a venipuncture site 11 by using an I.V. catheter 8 to insert the catheter C into the vein of a patient.

The I.V. set tubing T is then connected in a fluid tight seal with the catheter C to facilitate the administration of fluid therapy in the manner as previously described. More particularly, the healthcare provider attaches the I.V. set tubing T to the catheter 8 by sliding the nut N along the plastic connector 9 and into engagement with the head H. The nut is then rotated to lock the I.V. set tubing T to the catheter 8 as been seen in FIG. 24.

With the I.V. set tubing T so attached to the catheter 8, the healthcare provider removes the sheet of protective covering 17 from the underside of the securement 12 to provide access to the interior of the cover 14.

Next, the vault 24 is positioned over the venipuncture site 11 in an aligned manner so that the connector 9 is disposed within the proximal portion 15 and against the partition or interior wall 18 and the I.V. set tubing T aligned in the tube access slot 13 of the securement 12, the tube receiving stop 52 of the front wall 30 and the tube receiving slot 19 of the internal wall 18. With the vault 24 and the tubing T so aligned, the vault 24 of the site protector 10 is pressed against the skin of the patient. In this regard, the unprotected adhesive surfaces 136A and 136B uncovered when the cover 17 was removed secures the site protector 10 to the skin of the patient.

Next as best seen in FIG. 25, the healthcare provider grabs the tubing T extending from the access slot 13 toward the I.V. set in one hand and pulls the tubing T upwardly through the tubing access slot 13 and further upward into the tube receiving stop 52 of the front wall 30, and further upward into the tube receiving slot 19 of the internal wall 18, while simultaneously pushing down on the top of the vault 24 to hold it in place over the venipuncture site 11. This push and pull action allows a portion of the tubing T to be captured in the tubing receiving stop 20 of the interior wall 18 and in the tube receiving stop 52 of the front wall 30. This push pull action further forces the proximal end of the connector 9 to be wedged in a friction tight manner against the interior wall 18. In this regard, the connector 9 is wedged against the interior wall 18 in such a friction tight manner that dislodgement or movement of the I.V. connected catheter from the venipuncture site protector 10 is only possible by pulling the tubing downwardly through the tube access slot 13 of the securement 12. This of course is only made possible by removing the securement 12 from the venipuncture site 11.

Figure 26:
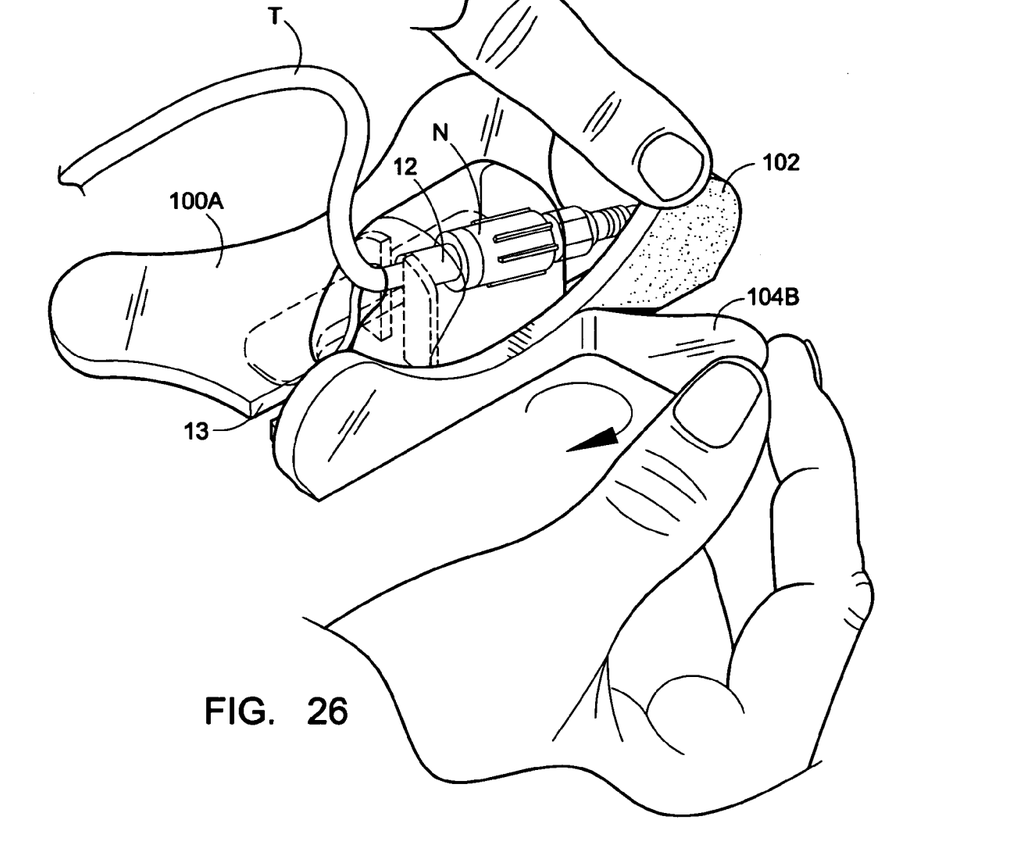

As best seen in FIG. 26, with the catheter 8 wedged within the venipuncture site protector 10, the health care provider lifts one of the wings 120A or 120B of the site protector 10 upward a sufficient distance so the protective cover 104A or 104B disposed on the underside of the wing 120A or 120B of the base securement 120 can be peeled away exposing the adhesive layer 102A or 102B of the wing 120A or 120B. The lifted lateral side is then pressed downward onto the skin of the patient to further secure the site protector 10 to the patient.

The health care provider then repeats the above mentioned procedure by lifting the other one of the wings 120A or 120B upward a sufficient distance so the remaining portion of the protective cover 104A or 104B disposed on the underside of the wing 120A or 120B can also be peeled away to expose the adhesive layer 102A or 102B. The other lifted wing 120A or 120B is then pressed downward onto the skin of the patient to further secure the site protector 10 to the patient.

From the foregoing, it should be understood by those skilled in the art, that I.V. connected catheter is disposed in the distal portion 15 of the site protector 10 and completely immobilized therein due do the friction tight engagement of the connector 9 with the interior wall 18 and the capturing of the I.V. tubing T within the tube receiving slot 19. In this regard, the tubing T cannot be dislodged from the site protector 10 except by exerting a sufficiently strong downward pulling action to dislodge the tubing T from both stops 20 and 52 so the tubing T can enter the slots 44 and 19, which in turn continue to exert a strong frictional resistance against the tubing so that dislodging the connector 9 from interior wall 18 and the front wall 30 is extremely difficult if not entirely impossible, unless the site protector 10 is first removed from the skin of the patient so the tubing T can first be pulled downward through the tube access slot 13 of the securement 12.

As a final step, as best seen in FIG. 1, any excess tubing associated with the I.V. set T can then be taped to the hand of the user by using a non skin irritating tape 21.

Considering now the venipuncture protector 10 in still greater detail, as best seen in FIG. 2-3, the cover 14 is composed of essentially two regions or portions. A proximal tube receiving portion 16 that protects and covers the IV set tubing, and a distal catheter receiving portion 15 that covers at least a portion of the catheter. The two portions 15 and 16 are separated by the internal wall 18.

Covering the distal portion is a vault 24. The distal end of the vault culminates in an arch 27 forming an opening 28. The proximal end of the vault 24 is integrally formed with the wall 30, which slopes downward from the proximal end of the vault 24 towards the securement 12 at an angle α relative to the securement. In one embodiment, the angle α is between about 30° and about 70°. In another embodiment, the angle is between about 40° and about 60°. In yet another embodiment, the angle is about 50°.

As shown in FIGS. 1, 24, 25 and 26, the roof of the vault 24 forms a tudor arch, which has a curvature resembling a semi-ellipse. Alternatively, the roof can form a bell arch in the shape of a semicircle, or it can have a rectangular, square or other similar shape. The opening 28 can have a shape that corresponds to the shape of the roof of the vault 24.

The opening 28 is formed by the arch 27. The opening 28 lies on a vertical plane that is substantially perpendicular to the securement 12 and the flanges 22A and 22B when the securement and flanges lie on a horizontal plane.

Another important feature of this embodiment of the present invention is that the roof of the vault 24 is high enough to accommodate typical catheter bodies. As mentioned earlier, the overall length, height and width dimensions of an I.V. connected catheter are standardized in the medical industry. In one embodiment, the height of the vault from the roof of the vault to the flanges 22A and 22B and securement 12 is between about 10 mm and about 20 mm. In another embodiment, the height of the vault is between about 12 mm and about 18 mm. In another embodiment, the height of the vault is about 15 mm. Also, the roof of the vault is substantially parallel with the flanges 22A and 22B and the securement 12 when the securement is in a horizontal plane. The length of the distal catheter receiving portion 15 is between about 15 mm and about 25 mm in one embodiment, between about 18 mm and about 22 mm in another embodiment, and between about 19 mm and about 20 mm in yet another embodiment.

Considering now the method of making the venipuncture protector 10 with reference to FIGS. 10-22, the method begins by first preparing a sheet of stock material 110 having a single adhesive surface that is protected by a wax paper covering. In this regard, the sheet of stock material 110 is prepared by providing a thin sheet of plastic material 100 having an upper surface area and a lower surface area as best seen in FIG. 10. The thin sheet of plastic material has a generally rectangular shape and a thickness of between about 3 mils and about 8 mils. The sheet of plastic material 100 is selected to have a sufficient surface area to be conformed into a desired shape corresponding to a desired securement shape, such as the securement shapes illustrated in FIGS. 5A-8.

Next, the lower surface area of the sheet of plastic material 100 is coated with a thin layer of non-skin irritating adhesive 102, which in turn, is immediately covered with a thin sheet of covering material 104. The covering material 104 is selected to have a surface area that corresponds to the surface area of the thin sheet of plastic material 100 and is provided to protect the adhesive 102 from exposure to objects during the manufacturing process.

The prepared sheet of stock material 110 is then stamp cut into any one of the desired securement shapes previously mentioned or any other shape that would be desired. For example the prepared sheet of stock material 110 is stamp cut into a dual winged shape to form a securement base 120 as best seen in FIGS. 5A and 11.

The process of making the dual wing shaped securement base 120 begins by first cutting the sheet of prepared material 110 into an overall desired securement pattern of dual wings 120A and 120B, such as best seen in FIG. 11. Next, the dual wings are separated by removing a center portion and forming an elliptical hole between the wings 120A and 120B, with the wings converging towards each other but separated by channels 108A and 108B.

Next a plurality of aeration holes are stamp cut through the sheet of stock material 110. The aeration holes are equally spaced apart and positioned to be at about adjacent each of the corners of the wings 120A and 120B. Although the method of preparing the wings 120A and 120B with the holes has been described in individual stamp cutting steps, those skilled in the art will appreciate that the dual wing shaped base 120 can be prepare in a single stamp process as well.

Figure 14:
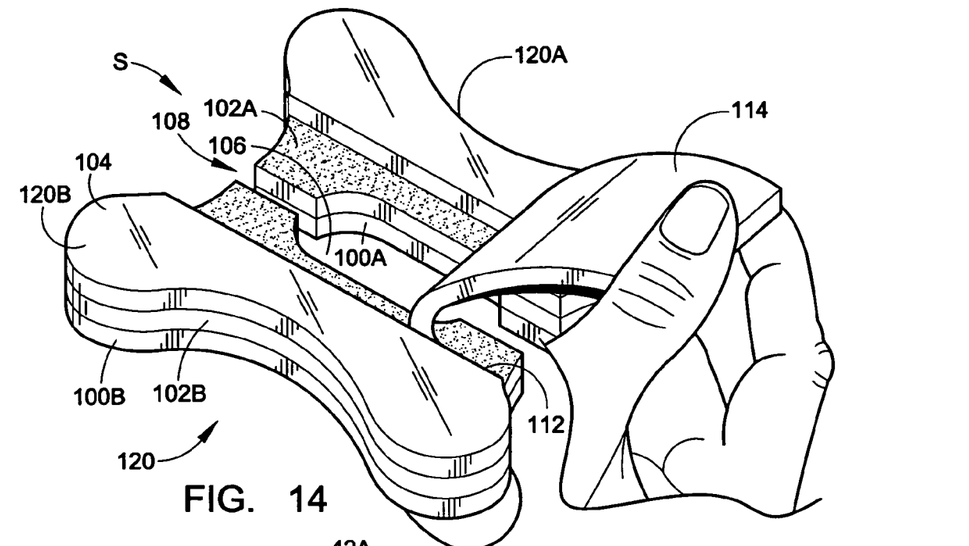

Next, as illustrated in FIG. 14, opposing pieces 114 of the covering material 104A and 104B whose lateral edges are defined by the score lines 112 are removed to form a step within the bottom of the wings 120A and 120B. This step also exposes the adhesive layer 102A and 102B that surrounds the hole 106 and the access channels 108A and 108B.

Figure 15:
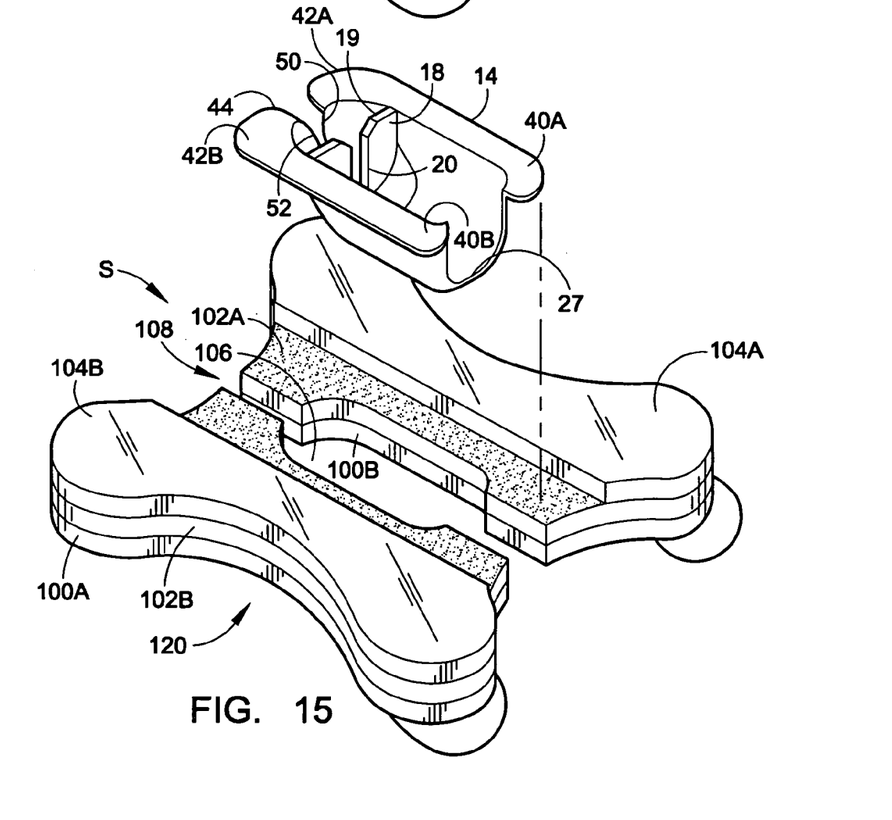

As best seen in FIG. 15, the method of making the venipuncture protector 10 continues by inverting the cover 14 and then placing the cover 14 into the oval shaped hole 106 between the two wings 120A and 120B so that the access channel 44 of the cover 14 is aligned with the access channel 108A. As the cover 14 is dropped into the hole 106, the upper surface area of its flange 22A and 22B are secured by the adhesive layer 102A and 102B to the base wings 120A and 120B respectively.

Figure 16:
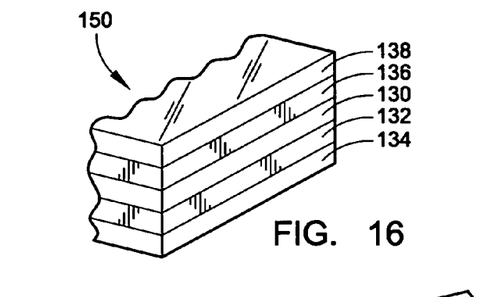

Next another sheet of stock material 150 having two adhesive surfaces with each surface being protected by a wax paper covering is provided. In this regard, the sheet of stock material 150 is prepared by providing a thin sheet of plastic material 130 having an upper surface area and a lower surface area as best seen in FIG. 16. The thin sheet of plastic material 130 has a generally rectangular shape and a thickness of between about 3 mils and about 8 mils. The sheet of plastic material 130 is selected to have a sufficient surface area to be conformed into a desired shape corresponding to a surface area of the cover 14. For example, in one embodiment, the plastic material 130 is stamp cut into a two piece configuration forming opposing pieces 160A and 160B separated by a hole 162 and channels 164A and 164B, as best seen in FIG. 17. In another embodiment, as seen in FIG. 17 the plastic material 130 is stamp cut into a single piece configuration that has a hole 162 separating two arms that are connected at one end, thus forming only a single channel 164.

Next, the lower surface area of the sheet of plastic material 130 is coated with a thin layer of adhesive 132, which in turn, is immediately covered with a thin sheet of covering material 134. The covering material 134 is selected to have a surface area that corresponds to the surface area of the thin sheet of plastic material 130 and is provided to protect the adhesive 132 from exposure to objects during the manufacturing process.

Next, the upper surface area of the sheet of plastic material 130 is coated with a thin layer of adhesive 136, which in turn, is immediately covered with a thin sheet of covering material 138. The covering material 138 is selected to have a surface area that corresponds to the surface area of the thin sheet of plastic material 130 and is provided to protect the adhesive 136 from exposure to objects during the manufacturing process.

Figure 19:
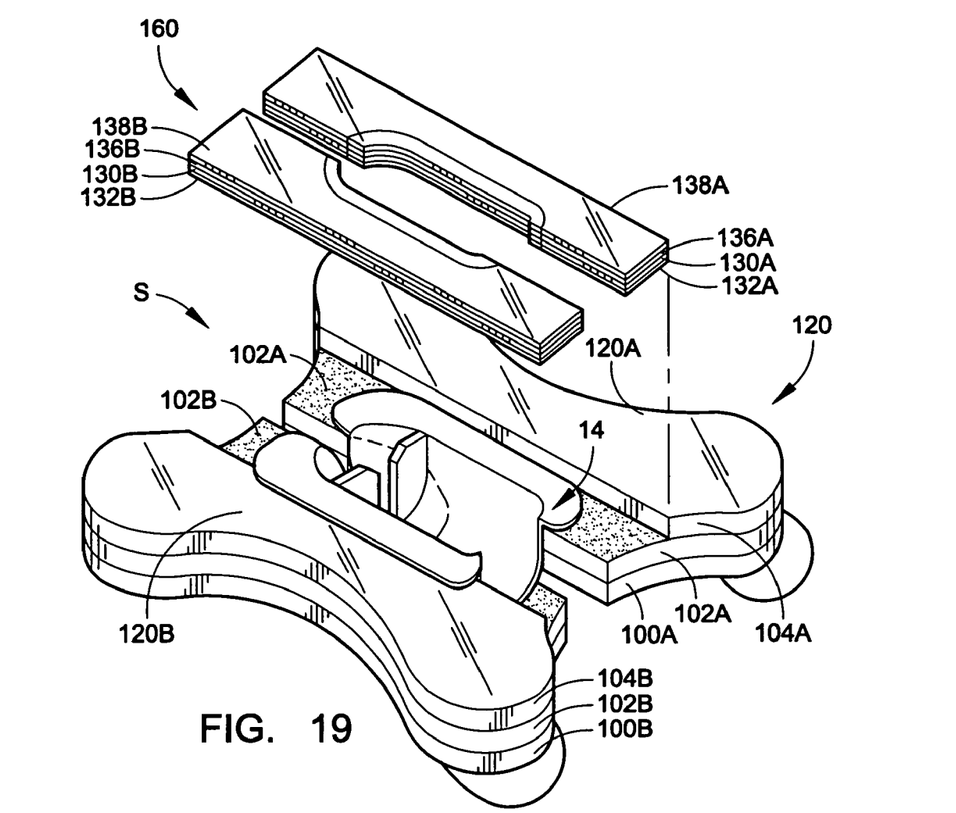

The prepared sheet of stock material 150 is then stamp cut into a two piece plug 160A and 160B (FIGS. 19 and 17) that substantially conforms to the shape of the cover 14 as seen in a bottom plane view but with a surface area that is slightly larger. As best seen in FIG. 19 the two piece plug 160A and 160B has sufficient width, height and depth dimensions to be received in and to fill the void or space S that was created when the pieces 114 of the covering material was removed from the base 120. As best seen in FIG. 19, the two piece plug 160A and 160B forms a hole 162 that correspond in shape to the hole 106 and two access channels 164A and 164B that correspond in shape to the access channel 108A and 108B.

Figure 18:
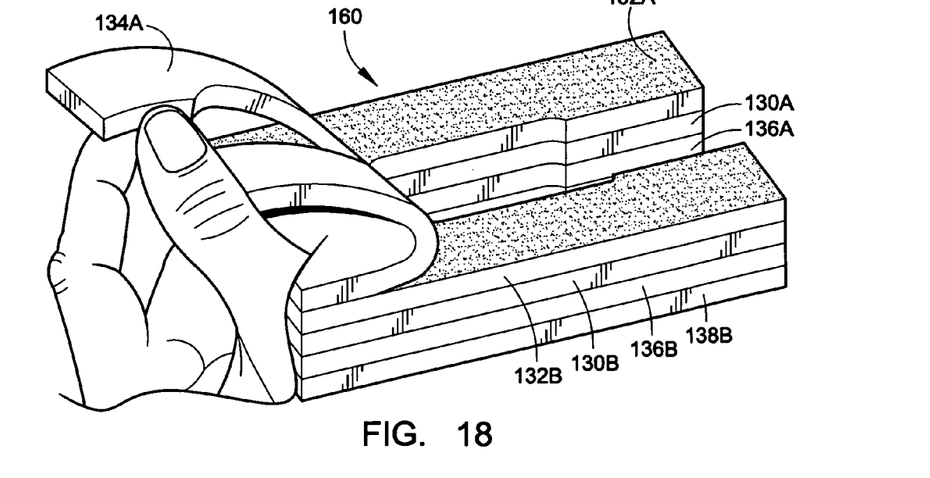

Next as best seen in FIG. 18, the plug 160A and 160B is inverted to expose the protective cover 134A and 134B. The protective cover 134A and 134B disposed on the lower adhesive layer 136A and 136B is then removed, exposing the adhesive layer 136A and 136B.

The plug 160A and 160B is then again inverted as best seen in FIG. 19, and moved into overlaying engagement with the exposed flanges 22A and 22B of the cover 14 that was previously mounted to the base 120. In this regard, the plug 160A and 160B is moved into the space S and pressed against the undersurface of the cover 14 and against the base 120 to secure the cover 14 between the base 120 and the plug 160A and 160B. In short then, the plug 160A and 160B is utilized to cover and secure the cover 14 to the base 120.

Figure 20:
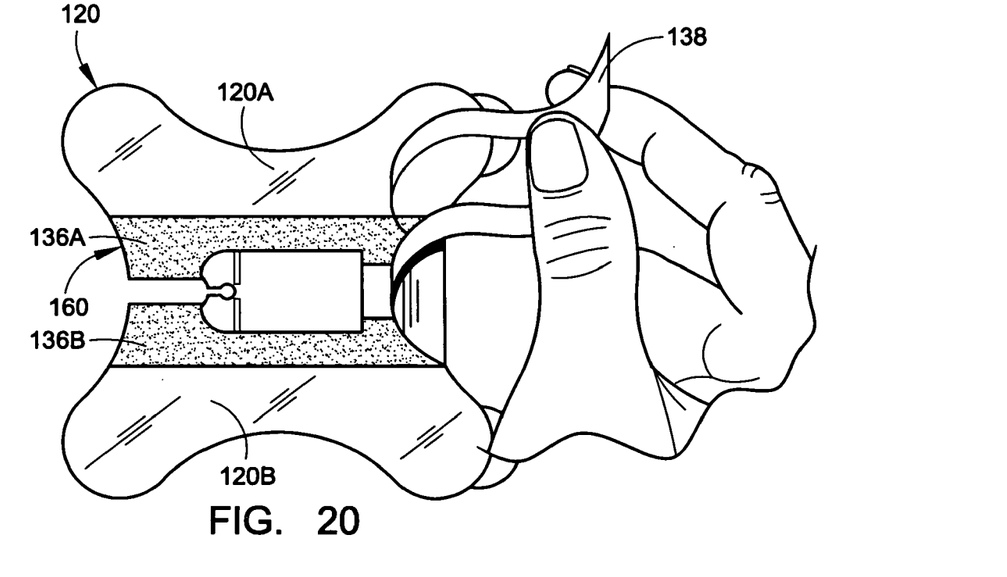

Next, as best seen in FIG. 20, the protective sheet 138A and 138B disposed on the upper layer of adhesive material 136A and 136B is removed, exposing the adhesive material 136A and 136B.

As best seen in FIG. 21, the method of making the venipuncture protector 10 continues by providing another sheet of protecting covering, such as a wax paper covering 17. In this regard a stock sheet of wax paper is stamp cut into a desired cover shaped form. The desired cover shaped form is generally rectangular having a width dimension to overlay the exposed adhesive surface 136A and 136B of the stock material 160A and 160B and part of the base 120. The length dimension of the wax paper covering 17 is slightly greater than the length dimension of the base 120.

Figure 22:
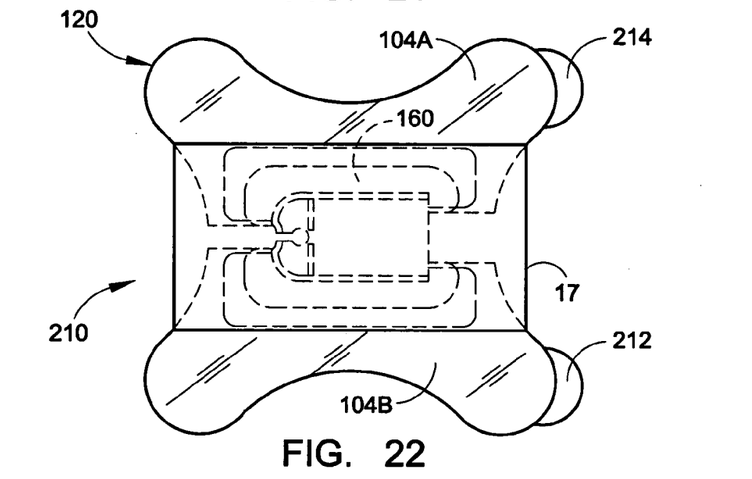
Figure 23:
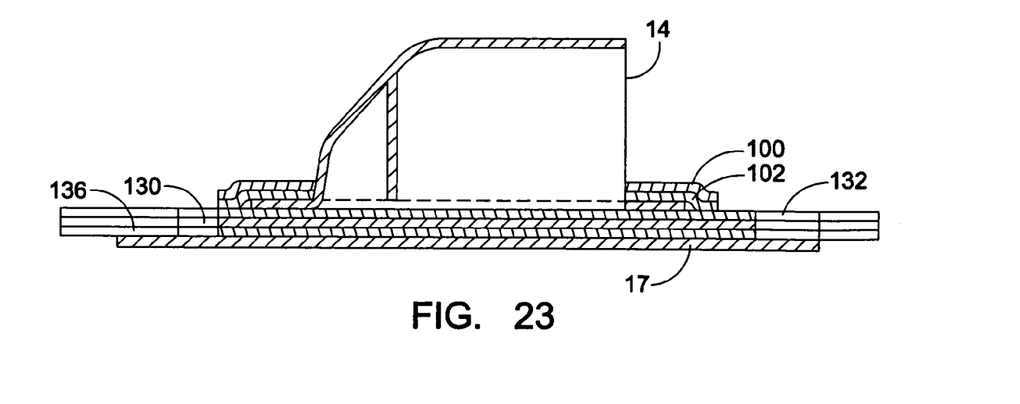
FIG. 23 is a cross sectional view of the venipuncture site protector of FIG. 21 taken along line 23-23.

As best seen in FIG. 22, another venipuncture protector 210 is shown and which is constructed in substantially in the same manner as the venipuncture protector 10 except the wax paper coverings 104A and 104B are each provided with a set of spaced apart lifting ears, such as the ears 212 and 214. The lifting ears 212 and 214 are sufficiently spaced apart from one another to not be covered by the wax paper covering 17.

Figure 6:
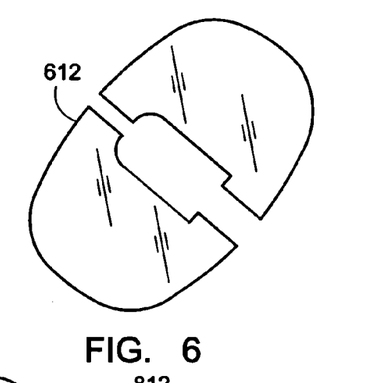
FIGS. 6-8 are illustrations of other still other types of securement configurations for use with the protective cover of FIG. 4.
Figure 7:
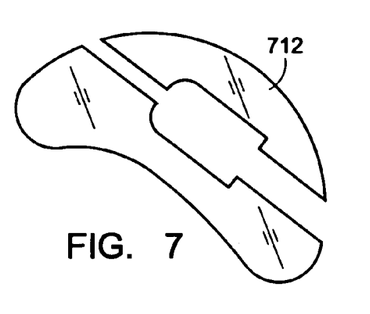
Figure 8:
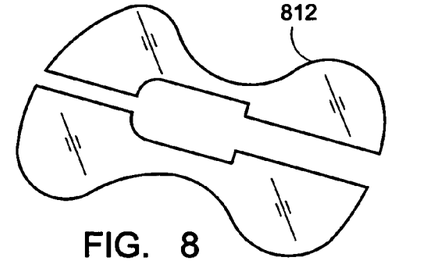

Referring now to the drawings and more particularly to FIGS. 6-8, there are illustrated other types of securements 612, 712, and 812. The securements 612, 712, and 812 are made and utilized in the same manner as securement 12. In this regard, there is no intention of limiting the scope of the present invention to any specific securement shape. In this regard, the securement shapes illustrated in FIGS. 6-8, as well as other types of securement shapes are contemplated within the true scope and spirit of the present invention.

Figure 9:
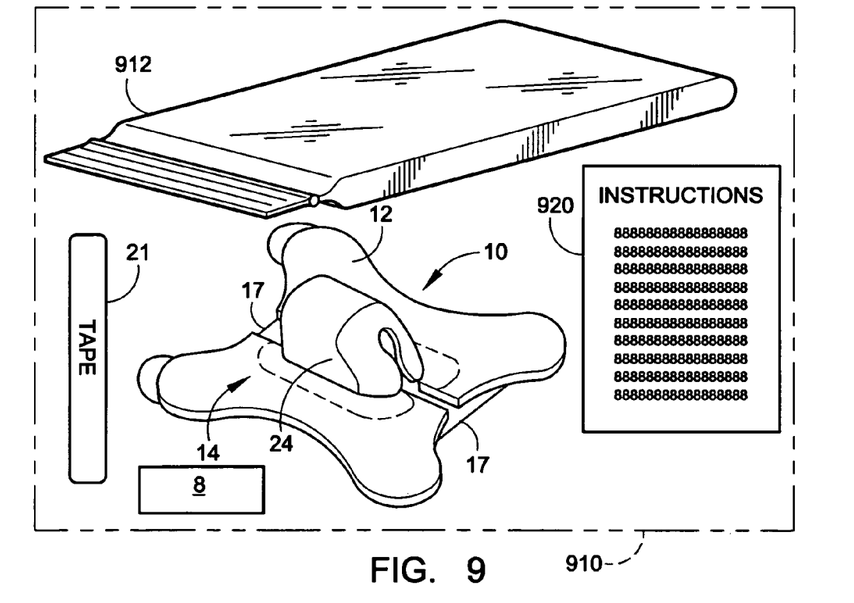
FIG. 9 is a venipuncture site protector kit, which is constructed in accordance with the present invention.

Referring now to the drawings and more particularly to FIG. 9 thereof, there is illustrated a site protector kit 910, which is constructed in accordance with another preferred embodiment of the present invention. The site protector kit 910 includes all of the necessary components to create a venipuncture site, such as the venipuncture site 11 and to protect that site 11 once a catheter C has been inserted into the vein of a patient. In this regard, the site protector kit 910 generally includes a sealed and sterilized packaging container 912 having disposed therein a venipuncture site protector 10, a set of instruction describing how to apply the venipuncture site protector 10 over a venipuncture site, a sealed and sterilized packaging container having a catheter 8 disposed therein, and a strip of tape 21 for securing any excess I.V. tubing to the area immediately adjacent to the venipuncture 11.

While particular embodiments of the present invention have been disclosed, it is to be understood that various different modifications are possible and are contemplated within the true spirit and scope of the appended claims. There is no intention, therefore, of limitations to the exact abstract or disclosure herein presented.

What is claimed:

1. A venipuncture site protector for a medical article comprising:
   a securement; and
   a cover mounted to said securement and having a lower entrance extending along a length of the cover, wherein a proximal end of said cover comprises a front wall with a tube receiving slot, at least a portion of the front wall being disposed directly below a portion of the medical article when the medical article is disposed in the tube receiving slot so as to support the portion of the medical article above a patient's skin, and a distal end of said cover comprises an arch that forms an opening that lies on a vertical plane that is substantially perpendicular to the securement, the opening being sized so that at least a portion of the medical article extends through the opening, and an internal wall spaced apart from the tube receiving slot and the front wall, projecting inwardly from the cover and defining an access channel, wherein the tube receiving slot, the access channel, and the opening are all open to the lower entrance to allow at least ingress of the medical article upwardly through the lower entrance and into the tube receiving slot, the access channel, and the opening, and wherein the internal wall is configured to contact the medical article when the medical article is disposed in the access channel so as to inhibit longitudinal movement of the medical article in at least one direction relative to the protector.

2. The venipuncture site protector of claim 1, wherein the internal wall separates the cover into a catheter receiving portion and a tube receiving portion.

3. The venipuncture site protector of claim 2, wherein the access channel is in substantial alignment with the tube receiving slot of the front wall.

4. The venipuncture site protector of claim 3, wherein the tube receiving slot of the securement is in substantial alignment with the tube receiving slot of the cover and the tube access channel of the internal wall.

5. The venipuncture site protector of claim 1, wherein the arch is in the shape of a tudor arch.

6. The venipuncture site protector of claim 1, wherein the arch is in the shape of a bell arch.

7. The venipuncture site protector of claim 1, wherein the front wall is sloped at an angle relative to the arch.

8. The venipuncture site protector of claim 2, wherein the catheter receiving portion of the cover forms a vault having any one of a barrel shaped roof, semi-elliptical roof, or rectangular roof.

9. The venipuncture site protector of claim 8, wherein the roof of the vault is substantially parallel to the securement and substantially perpendicular to the arch.

10. The venipuncture site protector of claim 8, wherein the front wall is sloped at an angle relative to the roof of the vault.

11. The venipuncture site protector of claim 1, wherein a distance between a top of the arch and the securement is approximately fifteen millimeters.

12. The venipuncture site protector of claim 1, wherein the cover comprises a flexible material.

13. The venipuncture site protector of claim 3, wherein said cover includes a flange having a tube receiving slot that is in substantial alignment with the tube receiving slot of the cover and the tube access channel of the internal wall.

14. The venipuncture site protector of claim 2, wherein said catheter receiving portion forms a space that is substantially larger than a space formed by the tube receiving portion, said catheter receiving portion being dimensioned to receive therein an I.V. connected catheter.

15. The venipuncture site protector of claim 1, wherein the tube receiving slot of the cover terminates in a tube-anchoring stop.

16. The venipuncture site protector of claim 3, wherein the access channel of the internal wall terminates in a tube-anchoring stop.

17. The venipuncture site protector of claim 1, wherein the portion of the medical article supported by the tube receiving slot is a tube.

18. The venipuncture site protector of claim 1, wherein at least a portion of the tube receiving slot has a smaller width than a diameter of the portion of the medical article inserted into the tube receiving slot.

19. The venipuncture site protector of claim 15, wherein a maximum width of the tube-anchoring stop is greater than a minimum width of the tube receiving slot.

\* \* \* \* \*